US012683003B2

(12) United States Patent
Lee et al.

(10) Patent No.: US 12,683,003 B2
(45) Date of Patent: Jul. 14, 2026

(54) THERAPY DATA MANAGEMENT SYSTEM

(71) Applicant: Bigfoot Biomedical, Inc., Milpitas, CA (US)

(72) Inventors: Kevin S. Lee, Milpitas, CA (US); Corydon A. Hinton, Oakland, CA (US); Alexandra Elena Constantin, San Jose, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 1131 days.

(21) Appl. No.: 17/302,792

(22) Filed: May 12, 2021

(65) Prior Publication Data

US 2021/0272669 A1     Sep. 2, 2021

Related U.S. Application Data

(62) Division of application No. 16/528,149, filed on Jul. 31, 2019, now Pat. No. 11,049,601.

(Continued)

(51) Int. Cl.
*G16H 20/17* (2018.01)
*A61B 5/145* (2006.01)
(Continued)

(52) U.S. Cl.
CPC ......... *G16H 20/17* (2018.01); *A61B 5/14532* (2013.01); *G16H 40/60* (2018.01); *A61M 5/1723* (2013.01); *G16H 10/60* (2018.01)

(58) Field of Classification Search
CPC ........ G16H 20/17; G16H 40/60; G16H 10/60; G16H 15/00; A61B 5/14532; A61M 5/1723
See application file for complete search history.

(56) References Cited

U.S. PATENT DOCUMENTS 8,123,717 B2     2/2012 Weinert et al.
2017/0173262 A1*  6/2017 Veltz ..................... G16H 20/17
(Continued)

OTHER PUBLICATIONS

International Search Report & Written Opinion for PCT Application No. PCT/US2019/044464, mailed on Oct. 28, 2019, 17 pages.
(Continued)

*Primary Examiner* — Rachelle L Reichert
(74) *Attorney, Agent, or Firm* — Goodwin Procter LLP

(57) ABSTRACT

A method for managing therapy data using computing nodes is disclosed. A computing node is associated with a blockchain identifying therapy data and features. The method includes: obtaining, by a first computing node from a first medical device, first therapy data, the first computing node being associated with a first blockchain; validating the first therapy data using features associated with the first blockchain; and in response to validating the first therapy data, adding the first therapy data to the first blockchain; receiving a request from a second medical device to obtain the first therapy data from the first block chain; providing, from the first computing node to the second medical device, and in response to receiving the request, the first therapy data to the second medical device, wherein the therapy data is used by the second medical device to provide a patient therapy recommendation.

20 Claims, 6 Drawing Sheets

Related U.S. Application Data

(60)  Provisional application No. 62/713,168, filed on Aug. 1, 2018.

(51)  Int. Cl.
  *A61M 5/172*          (2006.01)
  *G16H 10/60*          (2018.01)
  *G16H 40/60*          (2018.01)

(56)                References Cited

U.S. PATENT DOCUMENTS

| | | |
|---|---|---|
| 2018/0350451 A1 | 12/2018 | Ohnemus et al. |
| 2019/0108898 A1* | 4/2019 | Gulati .................... G16H 10/60 |
| 2019/0237176 A1 | 8/2019 | O'Brien et al. |

OTHER PUBLICATIONS

Griggs et al.: "Healthcare Blockchain System Using Smart Contracts for Secure Automated Remote Patient Monitoring", Journal of Medical Systems, Plenum Publishing Co, NY, USA; vol. 42, No. 7, Jun. 6, 2018, pp. 1-7.
Saravanan et al.: "SMEAD: A secured mobile enabled assisting device for diabetics monitoring," 2017 IEEE International Conference on Advanced Networks and Telecommunications Systems (ANTS), IEEE, Dec. 17, 2017, pp. 1-6.

* cited by examiner

200

700

702
Identify Abnormal Condition

704
Look up Ledger and Trace Events in Ledger

706
Identify Event that Potentially Caused Abnormal Condition

708
Identify Source Liable for Event

710
Take Action to Remediate if Necessary

THERAPY DATA MANAGEMENT SYSTEM

CROSS-REFERENCE TO RELATED APPLICATIONS

This application is a divisional application of U.S. application Ser. No. 16/528,149, filed Jul. 31, 2019, which claims priority to U.S. Provisional Application Ser. No. 62/713,168, filed on Aug. 1, 2018. The disclosure of both of the above applications is hereby incorporated in their entireties into this application.

TECHNICAL FIELD

This invention relates to a therapy data management system.

BACKGROUND

Diabetes mellitus is a chronic metabolic disorder caused by an inability of a person's pancreas to produce sufficient amounts of the hormone insulin such that the person's metabolism is unable to provide for the proper absorption of sugar and starch. This failure leads to hyperglycemia, i.e. the presence of an excessive amount of glucose within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Self-monitoring of blood glucose and the self-administration of insulin is the typical method for treating diabetes. In order to assist with this self-treatment, many diabetes-related devices and systems (e.g., blood glucose meters, insulin pumps, etc.) can generate therapy data and recommendations.

SUMMARY

This specification describes technologies for storing and managing therapy data using distributed ledger technologies. Such therapy data can be related to the use and operation of a therapy management system for administering therapy to a patient. For example, the therapy data can relate to administration of medicant by a medicant delivery system, such as an insulin delivery system for administering insulin to patients. A distributed ledger system is a decentralized data storage system with data replicated and synced across multiple computing nodes. A blockchain is a continuously growing list of data records linked and secured using cryptographic technology. A blockchain can be managed by a distributed ledger system with each computing node in the distributed ledger system adhering to a blockchain protocol for inter-node communication and new blocks validation.

Some embodiments of a distributed ledger system described herein are configured for multiple components in a therapy system to reliably record data of operations and contributions of each of the components to the therapy system, and permit for each of the components to trace such operations and contributions of all the components to the therapy system, thereby ensuring each of the components to operate and contribute to the therapy system the way it intends to do.

For example, a diabetic therapy system can include a variety of components associated with processes for treating diabetic conditions, such as one or more blood glucose meters (BGMs), one or more continuous glucose meters (CGMs), insulin pumps, insulin injection pens, insulin pen caps, mobile computing devices, cloud servers, and other suitable devices. When an event occurs with respect to a component, the component can record the event and/or data associated with the event onto a trusted ledger in a peer-to-peer system. For example, when an insulin injection pen cap detects a new insulin dosage that has been injected therefrom, the insulin injection pen cap can access the ledger and update it with the new insulin dosage and other suitable information, such as when the dosage was injected, when the pen cap receives the information about the dosage, when the pen cap records the information about the dosage, etc. The data being recorded on the ledger can further include data integrity (e.g., accuracy and consistency of the data) and/or authentication (e.g., to verify that it was indeed the component that recorded the data into the ledger).

All components in a therapy system can be nodes in a distributed ledger system. Alternatively, one or more components in a therapy system can be nodes in a distributed ledger system, while other components are not. At least one component in a therapy system can directly access, and record data on, a distributed ledger. Other components in the therapy system can access, and record data on, a distributed ledger through one or more intermediary devices which can directly access the distributed ledger. For example, a particular blood glucose meter which does not have capability of connecting to a broadband or cellular network can be connected to a mobile computing device via other wired or wireless interface (e.g., Bluetooth™), and the mobile computing device can receive measurement data from the blood glucose meter and record the measurement data and/or other associated data on the distributed ledger on behalf of the blood glucose meter. Such other associated data may include the fact that the mobile computing device received the measurement data from the particular blood glucose meter, the fact that the mobile computing device records the measurement data on behalf of the particular blood glucose meter, the time of transmission and/or reception of the measurement data, etc.

In addition, the data to be recorded on a distributed ledger can be transmitted, and/or recorded onto a distributed ledger, with message authentication code to ensure data integrity and authentication of components in the system. Various cryptographic signatures can be used. For example, a manufacturer of a component may generate a pair of private and public keys for a component (e.g., for a particular individual component or for all components of the same kind from the manufacturer), and keeps the private key and distribute the public key to other manufacturers or users to allow verification of the data that come from the claimed source (e.g., the particular component). In some implementations, a hash-based message authentication code (HMAC) can be used which involves a cryptographic hash function and a security cryptographic key. Other message authentication code or cryptographic signature schemes can be used in other implementations.

Some embodiments of a distributed ledger system described herein can provide component manufacturers with improved confidence with their partners (e.g., other manufacturers, healthcare practitioners, etc.) and allow interoperability and safety between different components provided by different manufacturers. Further, the distributed ledger system can permit for each entity (e.g., component manufacturer, healthcare practitioner, etc.) to objectively determine liability for a particular issue (e.g., abnormal condition) identified from the system or from a patient who uses the system. By way of example, such an issue may include discrepancy in data records between two different components. The distributed ledger can maintain all relevant data from all the components in the therapy system, and allow each party to trace the record to identify any abnormal behavior or suspicious operation from one or more components in the system. Such identification of abnormal behavior or suspicious operation of components can be used to identify a liable component or party (e.g., manufacturer, supplier, healthcare practitioner, user, etc.) and properly remediate the issue.

In general, one innovative aspect of the subject matter described in this specification can be implemented in a method for managing therapy data for a diabetic therapy system with a distributed ledger. The diabetic therapy system may include a plurality of components. The method may include detecting, at a first component in the therapy system, an event associated with the first component; updating, using the first component, a ledger with data representative of the event to generate an updated distributed ledger; validating, using one or more second components in the therapy system, the data based at least part on therapy data recorded in the distributed ledger; and generating, using the one or more second components, the updated distributed ledger, the updated distributed ledger including the data as part of the therapy data.

The foregoing and other implementations can each optionally include one or more of the following features, alone or in combination. In particular, the data representative of the event may include information about a measurement detected by the first component. The information may include at least one of a measurement value obtained by the first component, a time of the measurement being obtained, identification of the first component, a component to which the measurement is transmitted, and a time of the measurement being transmitted. The measurement value may include at least one of an amount of insulin injected, a blood glucose level, and an amount of carbohydrate recorded as ingested. The data representative of the event may include information about operation of the first component, the operation of the first component including a medicant injection by the first component, glucose level detection by the first component, user control inputs on the first component, user settings on the first component, and user interactions with a user interface of the first component. The first and second components may include at least one of a blood glucose meter, a continuous glucose meter, an insulin pump, an insulin injection pen, an insulin pen cap, a mobile computing device, and a cloud server. The method may further include receiving, at one of the first and second components, a request for the therapy data recorded in the distributed ledger; retrieving, at the one of the first and second components, the therapy data in response to the request; identifying, at the one of the first and second components, an event from the therapy data, the event having potentially caused an abnormal condition that occurred in the therapy system; identifying, at the one of the first and second components, a suspicious component associated with the identified event in the therapy system; and generating, at the one of the first and second components, a notification for informing a user of an action to take to remediate the abnormal condition. The method may further include transmitting, from the one of the first and second components, a signal to the suspicious component, the signal usable by the suspicious component to stop its operation.

Another innovative aspect of the subject matter described in this specification can be implemented in a distributed ledger system for a diabetic therapy system. The system may include a plurality of components, each including a data processing apparatus and a memory device storing instructions that when executed by the data processing apparatus cause the component to perform various operations. The operations may include detecting an event associated with the component; updating a ledger with data representative of the event to generate an updated distributed ledger; validating the data based at least part on therapy data recorded in the distributed ledger; and updating ledgers of the one or more second components to generate the updated distributed ledger. The updated distributed ledger includes the data as part of the therapy data.

The foregoing and other implementations can each optionally include one or more of the following features, alone or in combination. In particular, the operations may further include receiving a request for the therapy data recorded in the distributed ledger; retrieving the therapy data; identifying an event from the therapy data, the event having potentially caused an abnormal condition that occurred in the therapy system; identifying a suspicious component associated with the identified event in the therapy system; and generating a notification for informing a user of an action to take to remediate the abnormal condition. The operations may further include transmitting a signal to the suspicious component, the signal usable by the suspicious component to stop its operation.

Yet another innovative aspect of the subject matter described in this specification can be implemented in a method for managing therapy data using a plurality of computing nodes, wherein each of the plurality of computing nodes is associated with a respective blockchain that identifies therapy data and that is associated with a plurality of features, the method including: obtaining, by a first computing node of the plurality of computing nodes from a first medical device, first therapy data, the first computing node being associated with a first blockchain; validating the first therapy data using at least one of the plurality of features associated with the first blockchain; and in response to validating the first therapy data using at least one of the plurality of features associated with the first blockchain, adding the first therapy data to the first blockchain; receiving a request from a second medical device to obtain the first therapy data from the first block chain; providing, from the first computing node to the second medical device, and in response to receiving the request, the first therapy data to the second medical device, wherein the therapy data is used by the second medical device to provide a patient therapy recommendation.

The foregoing and other implementations can each optionally include one or more of the following features, alone or in combination. In particular, one embodiment includes all the following features in combination. The first and second medical devices are the same medical device. Validating the first therapy data using at least one of the plurality of features associated with the particular blockchain comprising: in response to obtaining the first therapy data, broadcasting, by the first computing node to at least one of the plurality of computing nodes other than the first computing node, the first therapy data, and verifying, by the at least one of the plurality of computing nodes other than the first computing node, that the first therapy data are valid. Verifying, by the at least one of the plurality of computing nodes other than the first computing node, that the first therapy data are valid comprising: obtaining a first value for at least one of the plurality of features associated with the first blockchain, identifying a second blockchain associated with the at least one of the plurality of computing nodes other than the first computing node, obtaining a second value for at least one of the plurality of features associated with the second blockchain, and comparing the first value to the second value. The first value is a nonce value for the first blockchain and the second value is a nonce value for the second blockchain. The medical device includes a glucose sensor that detects glucose or another analyte in interstitial fluid, and wherein the therapy data includes blood glucose level. The method further includes: obtaining, by the first computing source from the medical device, second therapy data; determining, by the first computing source, whether the second therapy data are within a range from a reference value; in response to a determination that the second therapy data are out of the range from the reference value, providing, by the first computing source to the medical device or a control device of the medical device, a signal that is configured to stop the medical device. The plurality of blockchains respectively associated with the plurality of computing nodes identify the same therapy data.

Yet another innovative aspect of the subject matter described in this specification can be implemented in a method for managing therapy data using a plurality of computing nodes, wherein each of the plurality of computing nodes is associated with a respective blockchain that identifies therapy data and that is associated with a plurality of features, the method comprising: obtaining, by a first computing node of the plurality of computing nodes from a first medical device, first therapy data, the first computing node being associated with a first blockchain; validating the first therapy data using at least one of the plurality of features associated with the first blockchain; and in response to validating the first therapy data using at least one of the plurality of features associated with the first blockchain, adding the first therapy data to the first blockchain; receiving a request from a mobile computing device to obtain the first therapy data from the first block chain; providing, from the first computing node to the mobile computing device, and in response to receiving the request, the first therapy data to the second medical device, wherein the therapy data is used by the second medical device to provide a patient therapy recommendation.

The subject matter described in this specification can be implemented in particular implementations and can result in one or more of the following advantages. Compared to a centralized system, a therapy data management system that has a distributed ledger system improves data security. In particular, the therapy data management system includes multiple distributed computing nodes and the distributed computing nodes each store the same blockchain. Since the therapy data is stored in the blockchain, even if one of the distributed computing nodes is compromised and the therapy data in the compromised computing node is changed, other uncompromised computing nodes can safely store the therapy data in their blockchains to allow the correct therapy data to be reliably retrieved and used in the administration of therapy.

Moreover, when the therapy data management system receives new therapy data, the therapy data management system can verify whether the new therapy data are valid by comparing the new therapy data to the therapy data already stored in the therapy data management system. In particular, the therapy data management system stores the therapy data in multiple blockchains. Thus, the new therapy data have to be validated multiple times. This improves the reliability of the therapy data management system.

Further, distributed ledger systems described herein can permit for respective components to reliably record data associated with the components, and trace the operations and contributions of all the other components, thereby providing higher confidence among different partners (e.g., manufacturers, supplier, healthcare practitioners, etc.) and allowing interoperability and safety between different components provided by different manufacturers. In addition, distributed ledger systems described herein can permit for each party (e.g., component manufacturer, healthcare practitioner, etc.) to objectively identify which party is liable for a particular issue and allow proper remediation based on the identification.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

A therapy data management system can record and manage therapy data using distributed ledger technologies. A distributed ledger system is a decentralized data storage system with data replicated and synced across multiple computing nodes. A blockchain is a continuously growing list of data records linked and secured using cryptographic technology. A blockchain can be managed by a distributed ledger system with each computing node (e.g., each of at least some components in a therapy data management system) in the distributed ledger system adhering to a blockchain protocol for inter-node communication and new blocks validation.

In some implementations, a distributed ledger system decentralizes data storage as every computing node independently maintains an updated copy of the blockchain. Each computing node of the distributed ledger system independently validates new blocks, e.g., new therapy data, to be appended to the blockchain. A distributed ledger system can host decentralized applications that execute across multiple computing nodes.

Figure 1:
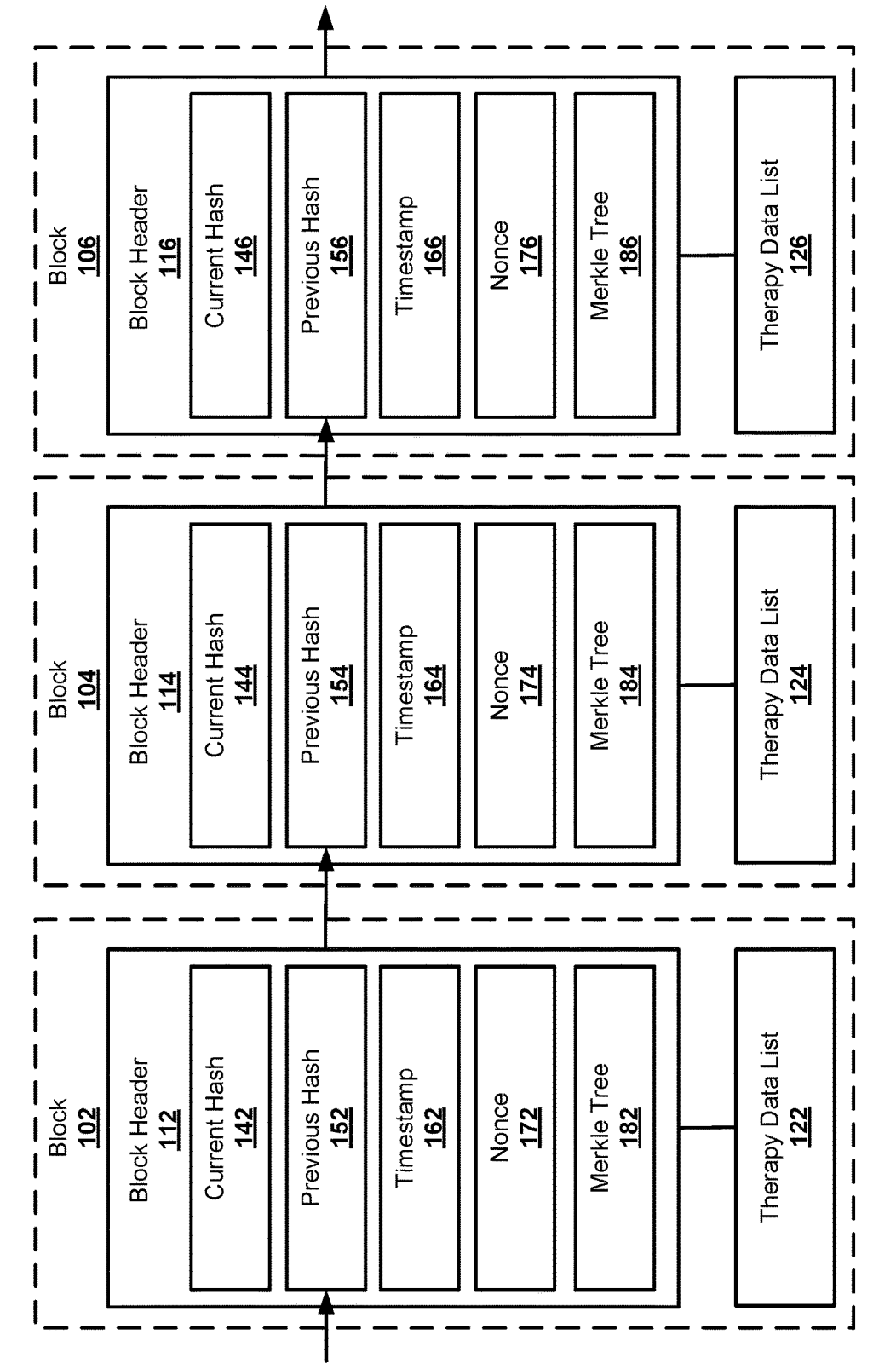
FIG. 1 illustrates an exemplary blockchain for a therapy data management system.

FIG. 1 illustrates an exemplary blockchain data structure for a therapy data management system. For example, a blockchain is an example distributed ledger system used with the therapy data management system described herein. A blockchain 100 includes multiple blocks and multiple lists associated with the blocks. For example, the blockchain 100 includes multiple blocks 102, 104, and 106. In this example, the blocks 102, 104, and 106 of the blockchain 100 are linked to each other. The block 102 is a starting block, i.e., a genesis block, and is linked to the next block 104. The block 104 is linked to both the block 102 and the block 106. The block 106 is linked to the block 104 and another block (not depicted) that is appended to the block 106. As a result, the blockchain 100 includes a chain of the blocks 102, 104, and 106 that are linked to each other. Other example embodiments can include more or less blocks than shown in the example of FIG. 1. For example, a blockchain could include hundreds or thousands of blocks. Each block in the blockchain 100 can include data representative of an event associated with a component (e.g., a therapy device) in a therapy system. By way of example, one of the blocks in the blockchain can include data about an insulin dosage injected to a patient from an insulin injection pen at a particular time on a particular date, and another block in the blockchain can include data about a blood glucose level of the patient which was measured by a blood glucose meter at another time on another date. Each block may include data representative of a plurality of events associated with one or more components in a therapy system.

In some implementations, a block can have a data structure including at least one block header and one therapy data list that is associated with the block header. For example, the block 102 includes a block header 112 and a therapy data list 122 that is associated with the block header 112, the block 104 includes a block header 114 and a therapy data list 124 that is associated with the block header 114, and the block 106 includes a block header 116 and a therapy data list 126 that is associated with the block header 116. In some implementations, a block can include multiple block headers and multiple therapy data lists. In these implementations, one block can be associated with one therapy data list, one block can be associated with multiple therapy data lists, or multiple blocks can be associated with one therapy data list.

A block header for a block, e.g., the block header 112 for the block 102, includes metadata describing various features of the block. For example, the metadata can include a current hash, a previous hash, a timestamp, a nonce, and a Merkle root. In some implementations, at least one of the features of the metadata can be represented as a string value.

In some implementations, metadata of a block header can include a current hash. For example, metadata of the block header 112 includes a current hash 142, metadata of the block header 114 includes a current hash 144, and metadata of the block header 116 includes a current hash 146. A current hash can include a digital identifier of the block. In particular, the current hash can include a unique digital identifier of the current block. For example, the current hash 142 can be a unique digital identifier of the block 102, the current hash 144 can be a unique digital identifier of the block 104, and the current hash 146 can be a unique digital identifier of the block 106. In some implementations, the current hash can be a cryptographic digital signature generated by feeding particular data into a cryptographic hash function. A cryptographic hash function is a special class of hash functions that maps data of arbitrary size to a bit string of a particular size. For example, the cryptographic hash function can have an output of a 32-bit string value. In some implementations, the current hash can be calculated by feeding block data, e.g., string values in a block header and a therapy data list, to a cryptographic hash function specified in a blockchain protocol. Where each block in the blockchain has unique block data, two different data cannot have the same hash value. Thus, a current hash associated with a particular block can be unique for that particular block in the blockchain.

In some implementations, metadata of a block header can include a previous hash. For example, metadata of the block header 112 includes a previous hash 152, metadata of the block header 114 includes a previous has 154, and metadata of the block header 116 includes a previous hash 156. A previous hash can include a hash pointer that points to the previous block. For example, the previous hash 152 is a hash pointer that points to the previous block (not shown) of the block 102, the previous hash 154 is a hash pointer that points to the previous block 102 and the previous hash 156 is a hash pointer that points to the previous block 104. In some implementations, where the block 102 is a starting block, i.e., a genesis block, that is generated by the blockchain protocol, the metadata of the block header 112 does not include any previous hash. As a result, all the blocks of the blockchain can be linked to each other using hashes. This blockchain design improves the security of data stored in a blockchain. For example, to compromise therapy data in the block 102 of the blockchain 100, a hacker would need to compromise all the blocks linked to the block 102. In this example, since the previous hash 156 in the block 106 points to the block 104 and the previous hash 154 of the block 104 points to the block 102, a hacker would need to compromise therapy data in the blocks 104 and 106 as well to compromise the therapy data in the block 102. Thus, the blockchain design provides improved security for therapy data stored in the blockchain. In particular, this blockchain design can be used to store and manage therapy data.

In some implementations, metadata of a block header can include a timestamp. For example, metadata of the block header 112 includes a timestamp 162, metadata of the block header 114 includes a timestamp 164, and metadata of the block header 116 includes a timestamp 166. A timestamp can identify the time at which the current block was added to the blockchain. In some implementations, computing nodes of the distributed ledger system can reference one or more dedicated time-reporting servers to record consistent timestamp across the distributed ledger system. In some implementations, the timestamp identifying the time at which the current block was added to the blockchain is used as part of the input to a cryptographic hash function to determine the current hash for a block.

In some implementations, metadata of a block header can include a nonce. For example, metadata of the block header 112 includes a nonce 172, metadata of the block header 114 includes a nonce 174, and metadata of the block header 116 includes a nonce 176. A nonce can represent an arbitrary random value that is used in the cryptographic hash function to control the hash output. In some implementations, to add a new block to a blockchain, a particular type of a computing node can determine a nonce value and repeatedly hash the therapy data in the new block until the hash output, i.e., the current hash of the new block, satisfies one or more specified conditions. For example, a condition for adding a new block to a blockchain can be that the hash output, i.e., the current hash of the new block, should have a particular string value.

In some implementations, metadata of the block header 112 includes a Merkle tree 182, metadata of the block header 114 includes a Merkle tree 184, and metadata of the block header 116 includes a Merkle tree 186. A Merkle tree can be a binary tree where every leaf node is a hash of a data block and every non-leaf node is a hash of its two child nodes. A Merkle root identifies the list of therapy data associated with each block. In some implementations, a Merkle root can represent a particular hash value. The particular hash value can be generated by feeding data in a therapy data list into a Merkle tree of a particular block. For example, the particular hash value can be the top hash value from multiple hash values generated by feeding data in a therapy data list into a Merkle tree of a particular block.

As described above, the blockchain 100 also includes multiple therapy data lists 122, 124, and 126. For example, the therapy data list 122 includes one or more therapy data associated with the block 102, the therapy data list 124 includes one or more therapy data associated with the block 104, and the therapy data list 126 includes one or more therapy data associated with the block 106. In some implementations, the therapy data in the therapy data list 122 are therapy data that was recorded at, or related to therapy that occurred, from the time at which the previous block (not shown) was added to the blockchain 100 to the time that is identified at the timestamp 162. The therapy data in the therapy data list 124 are therapy data that was recorded at, or related to therapy that occurred from the time at which the previous block 102 was added to the blockchain 100 to the time that is identified at the timestamp 164. The therapy data in the therapy data list 126 are therapy data that was recorded at, or related to therapy that occurred from the time at which the previous block 104 was added to the blockchain 100 to the time that is identified at the timestamp 166. For example, therapy data can be received when one computing node of the distributed ledger system sends therapy data to another computing node of the distributed ledger system. The therapy data in the therapy data lists 122, 124, and 126 can be described using elements including a sender address and/or other information for identifying the sender in the distributed ledger system, a receiver address and/or other information for identifying the receiver in the distributed ledger system, transferred therapy data, a timestamp of the therapy data, a unique therapy data ID, or a combination of these. In some implementations, the description elements can be represented as a string value. As described herein, the therapy data can include data (e.g., measurements, dosage, etc.) associated with a component in a therapy system, and/or one or more events resulting from operation of the component in the therapy system.

In some implementations, therapy data recorded in a blockchain include various data related to one or more components in a therapy system, such as one or more medical devices or control devices for the medical devices. For example, the therapy data includes measurements by sensors or setting data for an insulin pump. As another example, the therapy data includes data to identify particular medical devices. That is, data to identify that a particular medical device is a medical device approved by a government agency or a medical device registered by a user can be therapy data. As another example, the therapy data includes data related to the delivery for insulin (e.g., the delivery schedule, dosage, etc.). As another example, the therapy data includes data received from a patient or a caretaker. The therapy data will be described in greater detail with reference to FIGS. 3 to 5B.

In some implementations, therapy data can be received from various devices. For example, the therapy data can be directly received from components in a therapy system including medical devices such as sensors or control devices for the medical devices. As another example, the therapy data can be received from medical devices such as sensors through an intermediate device or third-party device such as a smartphone. That is, the third-party device receives the therapy data from the sensors and transfer the received therapy data to a therapy data management system.

Figure 2:
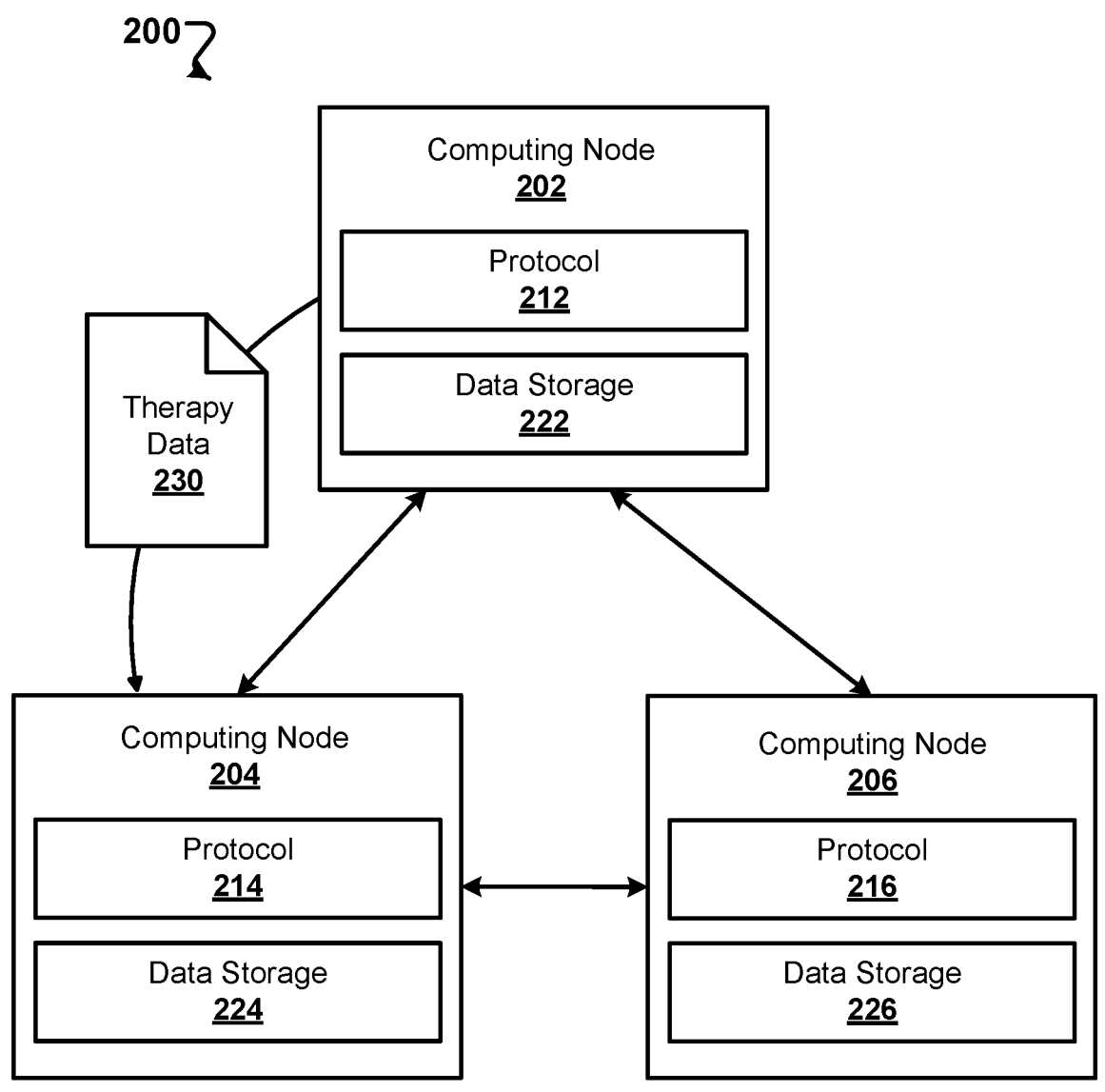
FIG. 2 illustrates an exemplary therapy data management system.

FIG. 2 illustrates an example therapy data management system. As illustrated in FIG. 2, the therapy data management system 200 can be a distributed ledger system that is a decentralized data storage system with data replicated and synced across multiple computing nodes. In a diabetic therapy system, for example, such computing nodes can include, or be associated with, one or more therapy components, such as one or more blood glucose meters (BGMs), one or more continuous glucose meters (CGMs), insulin pumps, insulin injection pens, insulin pen caps, etc., and/or one or more non-therapy components, such as mobile computing devices, cloud servers, and other suitable computing devices communicating with therapy or non-therapy components. A distributed ledger system is a network of computing nodes to maintain a blockchain, e.g., the blockchain 100 of FIG. 1, according to a particular blockchain protocol.

The therapy data management system 200 can include multiple computing nodes. For example, the therapy data management system 200 includes computing nodes 202, 204, and 206. In some implementations, each computing node is independent from another computing node and connected to every other computing node. In some implementations, computing nodes can be nodes associated with particular functions. For example, computing nodes can be mining nodes or data nodes. In some implementations, the computing nodes can be standalone computing devices such as servers, desktop computers, laptop computers, or other types of computing devices. In some implementations, multiple computing nodes can be implemented on a single computing device, such as a server. In some implementations, one computing node can be distributed across multiple computing devices, such as multiple network servers.

In some implementations, mining nodes can be a type of computing nodes in the therapy data management system that implement a blockchain protocol. For example, a mining node spends computing resources to validate other therapy data. The mining node calculates and determines a nonce value to satisfy specified conditions for adding a new block, i.e., adding the therapy data identified in the new block.

In some implementations, data nodes can be a type of computing nodes in the distributed ledger system that do not implement the full blockchain protocol. For example, a therapy data node does not spend computing resource to validate other therapy data, but rather relies on mining nodes for the task. A therapy data node functions exclusively to send and receive data in the distributed ledger system with other computing nodes in the distributed ledger system.

In some implementations, a computing node can include a protocol. For example, the computing node 202 includes a protocol 212, the computing node 204 includes a protocol 214, and the computing node 206 includes a protocol 216. A protocol can be a particular blockchain protocol that is executed by the computing node including the protocol. In some implementations, a protocol can be executed only by the computing node including the protocol. For example, the protocol 212 can be executed only by the computing node 202, but cannot be executed by other computing nodes 204 and 206. The protocol 212 can specify rules to manage a blockchain, e.g., the blockchain 100 in FIG. 1. For example, the rules specified in the protocol 212 can include one or more conditions for allowing a computing node to add a new block to the therapy data management system 200, the frequency of adding new blocks, and the type of data included in a block.

In some implementations, a computing node can also include a data storage for storing information of a blockchain. For example, the computing node 202 includes a data storage 222 for storing information of the blockchain, the computing node 204 includes a data storage 224 for storing information of the blockchain, and the computing node 206 includes a data storage 226 for storing information of the blockchain. In this example, the data storages 222, 224, and 226 store information of the same blockchain. That is, all the computing nodes 202, 204, and 206 in the therapy data management system 200 stores information about the same blockchain. Thus, even if one computing node, e.g., the computing node 202, is compromised, other computing nodes in the same system, e.g., the computing nodes 204 and 206, can validate compromised therapy data by comparing the compromised therapy data stored in the computing node 202 to the uncompromised therapy data stored in the computing nodes 204 and 206. Moreover, when the computing node 202 receives therapy data generated by a component (e.g., sensor), the therapy data management system 200 can verify whether the received therapy data is within a particular range from a reference by comparing the received therapy data to the therapy data stored in the computing nodes 204 and 206. If the received therapy data is out of the range, the therapy data management system 200 can determine that the component (e.g., the sensor) does not operate consistently.

In some implementations, therapy data in the distributed ledger system are initiated when a transfer of therapy data occurs. For example, the blockchain maintained in the distributed ledger system 200 can be a record of therapy data among computing nodes. In some implementations, the computing nodes 202, 204, and 206 can act as data nodes. For example, the computing nodes 202, 204, and 206 can send and receive therapy data as data nodes. In some implementations, the computing nodes 202, 204, and 206 can act as mining nodes. For example, the computing nodes 202, 204, and 206 can validate one or more new blocks added to the blockchain stored in the data storages 222, 224, and 226 of the therapy data management system 200.

The therapy data management system 200 can initiate recording of therapy data 230 by sending the therapy data 230 from one computing node (e.g., the computing node 202) to another computing node (e.g., the computing node 204). To record the therapy data 230 to all the blockchain stored in the data storages 222, 224, and 226, the computing node 202 broadcasts the therapy data 230 to other computing nodes 204 and 206 in the therapy data management system 200. When the computing node 204 receives the therapy data 230, the computing node 204 can verify that the therapy data 230 are valid therapy data. The computing node 204 can look into records in the existing blockchain stored in the data storage 224 to verify that the computing node 202 satisfies one or more conditions to send the therapy data 230. If the computing node 202 satisfies the condition, the computing node 204 initiates a mining process to add the therapy data 230 to the blockchain stored in the data storage 224 of the computing node 204.

Mining is a process in which a computing node spends computing resources to search for a particular nonce value, e.g., a particular string value, that causes the current hash to satisfy a particular condition. If the computing node calculates the valid nonce, the therapy data is added to the blockchain stored in the computing node after other computing nodes validate the proposed nonce value.

For example, where the computing node 204 performs a mining process to add the therapy data 230 to the blockchain stored in the data storage 224, the computing node 204 calculates and determines a particular nonce value using computing resources. When the computing node 204 determines a nonce value such that the current hash satisfies a particular condition, the computing node 204 broadcasts, to all the other computing nodes in the therapy data management system 200, e.g., the computing nodes 202 and 206, that the computing node 204 has determined the valid nonce value. In some implementations, the computing node 204 can broadcast to all the other computing nodes in the therapy data management system 200 other than the starting computing node, e.g., the computing node 202, that the computing node 204 has determined the valid nonce value. Once other computing nodes, e.g., the computing node 206, in the therapy data management system 200 receives the broadcasting, other computing nodes, e.g., the computing node 206, validate the proposed nonce value. If the proposed nonce value is validated by all the other computing nodes of the therapy data management system 200, the therapy data 230 is added to the blockchain in all the data storages 222, 224, and 226 in the therapy data management system 200.

Figure 3:
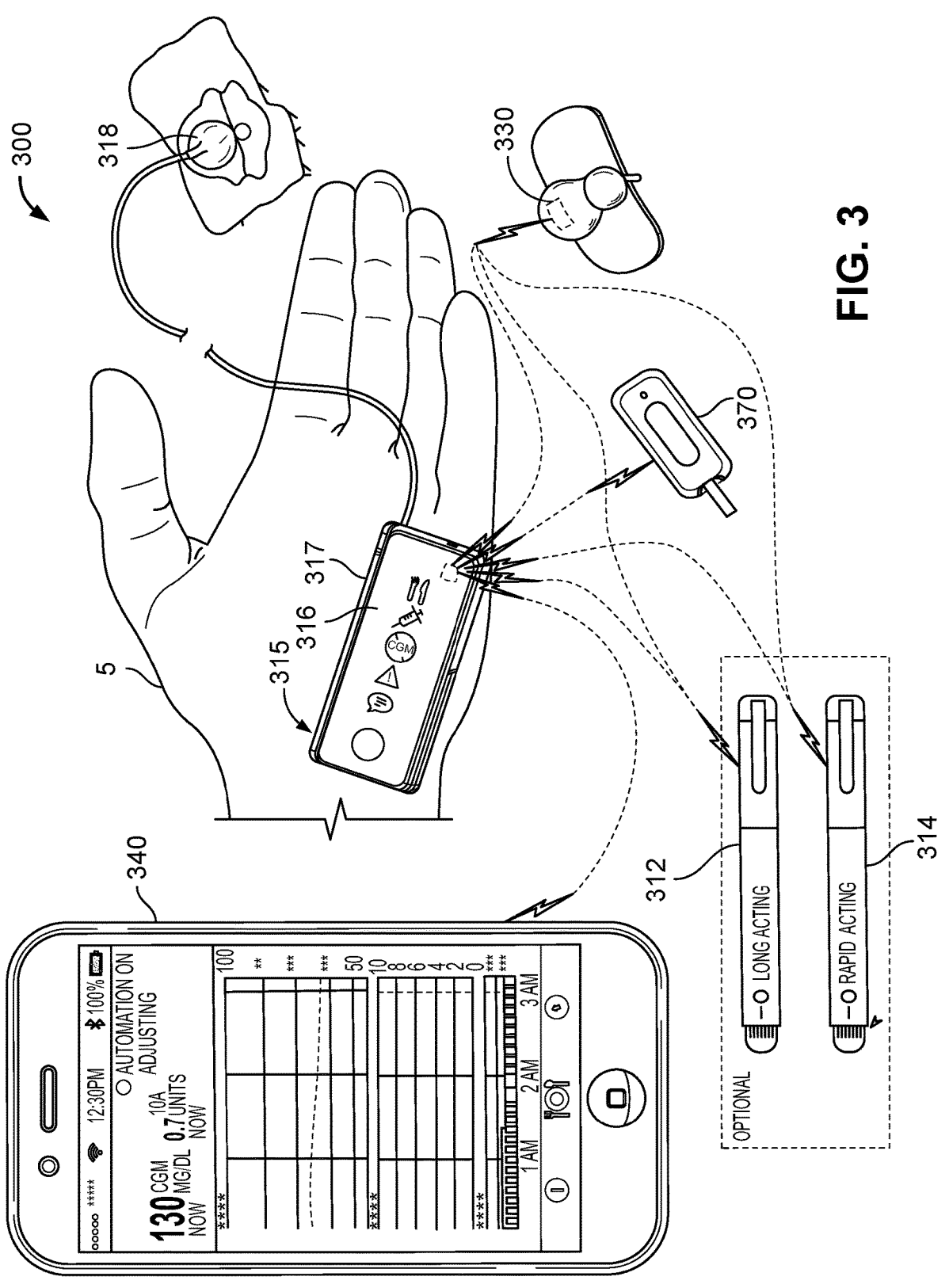
FIG. 3 illustrates an exemplary diabetes management system according to a first implementation.

FIG. 3 illustrates an exemplary therapy system that provides therapy data to a therapy data management system. For example, the therapy system may be a diabetes management system 300. The diabetes management system 300 can include a plurality of therapy related and/or non-therapy related components which can generate therapy data as described herein. For example, the diabetes management system 300 can include an insulin pump assembly 315 and a glucose sensor 330, which may be a continuous glucose monitor. As shown, the glucose sensor 330 is in wireless communication with insulin pump assembly 315. In some implementations, a glucose sensor can be in wired communication with insulin pump assembly 315. In some implementations, glucose sensor 330 can be a flash glucose monitor that is adapted to wirelessly transmit blood glucose values to insulin pump assembly 315 when it is interrogated by the insulin pump assembly 315. In some implementations not shown, the glucose sensor can be incorporated into an insulin pump assembly. As shown, the insulin pump assembly 315 can include a reusable pump controller 316 that forms part of the pump assembly. In some implementations, the reusable pump controller 316 is adapted to store a schedule of basal rates based on a time of the day. In some implementations, the reusable pump controller 316 is adapted to determine one or more basal delivery rates based on data from the glucose sensor 330 in combination with a user-specific dosage parameters that are stored according to a time of the day. In some implementations, the glucose sensor 330 can act as a controller adapted to communicate basal delivery rates to the insulin pump assembly 315 based on a schedule and/or based on current blood glucose data.

The insulin pump assembly 315, as shown, can include the reusable pump controller 316 and the disposable pump 317, which can contain a reservoir for retaining insulin. A drive system for pushing insulin out of the reservoir can be included in either the disposable pump 317 or the reusable pump controller 316. In some implementations, the drive system can be formed partially by the disposable pump 317 and partially by the reusable pump controller 316. The reusable pump controller 316 can include a wireless communication device, which can be adapted to communicate with a wireless communication chip in glucose sensor 330 and other diabetes devices in the system, such as those discussed below. For example, the reusable pump controller 316 can communicate with the glucose sensor 330 and other devices using near field communication (NFC), RF communication such as 433 RF radio communication, short distance communication (such as BLUETOOTH® based communication), Wi-Fi, or any other suitable wireless or wired communication protocol.

In some implementations, the insulin pump assembly 315 can be sized to fit within a palm of a hand 5. The insulin pump assembly 315 can include an infusion set 318. The infusion set 318 can include a flexible tube that extends from the disposable pump 317 of the insulin pump assembly 315 to a subcutaneous cannula that may be retained by a skin adhesive patch (not shown) that secures the subcutaneous cannula to the infusion site. The skin adhesive patch can retain the cannula in fluid communication with the tissue or vasculature of the person with diabetes (PWD) so that the medicine dispensed through the tube passes through the cannula and into the PWD's body. A cap device can provide fluid communication between an output end of an insulin cartridge (not shown) and the tube of infusion set 318.

The glucose sensor 330 (e.g., a continuous glucose monitor) can include a housing, a wireless communication chip, and a sensor shaft. The wireless communication chip can be contained within the housing and the sensor shaft can extend outward from the housing. In use, the sensor shaft can penetrate the skin of a user to make measurements indicative of the PWD's blood glucose level or the like. In some implementations, the sensor shaft can measure glucose or another analyte in interstitial fluid or in another fluid and correlate that to blood glucose levels.

For example, the glucose sensor 330 can generate therapy data based on the measurements. In some implementations, the measurements themselves can be therapy data. In some implementations, the glucose sensor 330 can transmit the therapy data to a therapy data management system, e.g., the therapy data management system 200 in FIG. 2. In some implementations, the glucose sensor 330 can transmit the therapy data to the pump assembly 315 and the pump assembly 315 can transmit the therapy data to a therapy data management system, e.g., the therapy data management system 200 in FIG. 2. Alternatively, an intermediate device, such as a mobile device 340, can communicate with the glucose sensor 330 and/or the pump assembly 315 to receive therapy data therefrom and transmit the therapy data to a therapy data management system.

In some implementations, the therapy data management system, e.g., the therapy data management system 200 in FIG. 2, can validate the therapy data using mining nodes of the therapy data management system. For example, the therapy data management system can validate whether the therapy data received from a device are within an expected range from a threshold. When the therapy data management system determines that the received therapy data are out of the range, the therapy data management system can send a warning signal to the device to prevent a user from using the device. In some implementations, when the therapy data management system determines that the received therapy data are out of the range, the therapy data management system can send a signal to the device or a control device of the device to stop the device. In some implementations, a device that provides the therapy data to the therapy data management system is required to sign the therapy data cryptographically. In these implementations, the signatures for the therapy data are verified in mining nodes of the therapy data management system.

In some implementations, the therapy data management system can determine whether the device that transmits the therapy data operates consistently by validating the therapy data. In these implementations, the therapy data management system can determine that a device operates inconsistently by validating the therapy data. Where different devices are provided from different manufacturers, for example, the glucose sensor 330 is provided by Company A and the pump assembly 315 is provided by Company B, the therapy data management system can identify which device between the glucose sensor 330 and the pump assembly 315 operates inconsistently. Thus, the therapy data management system can be used to determine which company should be liable for the damages caused by a possible malfunction of the device. The therapy data management system can also generate data that can be used to troubleshoot or improve the function of a device that is operating inconsistently. This information can be provided to a manufacturer or servicer of the device to provide for improvement of the device.

In some implementations, the therapy data management system can add the received therapy data to a blockchain of the therapy data management system as described with reference to FIG. 2. For example, referring to FIG. 2, when the computing node 202 receives the therapy data from the glucose sensor 330 or the pump assembly 315, the computing node 202 broadcasts the therapy data to other computing nodes, e.g., the computing nodes 204 and 206. Another computing node, e.g., the computing node 204, receives the therapy data and verifies that the therapy data are valid therapy data. If the computing node 204 verifies that the received therapy data are valid therapy data, the therapy data can be added to the blockchain stored in all the data storages 222, 224, and 226 in the therapy data management system 200. Once the therapy data are added to the blockchain, even if one of the computing nodes in the therapy data management system is compromised and the value of the therapy data are changed at a blockchain of one computing node in the therapy data management system, the changed value of the therapy data cannot be validated by other computing nodes because other computing nodes also stores the unchanged value of the therapy data. Thus, the therapy data management system improves the security of therapy data.

Additionally or alternatively, the system 300 may include another glucose monitoring device that may utilize any of a variety of methods of obtaining information indicative of a PWD's blood glucose levels and generating therapy data based on the information. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. The glucose monitoring device can generate therapy data based on the measurements. In some implementations, the measurements themselves can be therapy data. In some implementations, the glucose monitoring device can transmit the therapy data to a therapy data management system, e.g., the therapy data management system 200 in FIG. 2. In some implementations, the glucose monitoring device can transmit the therapy data to the reusable pump controller 316 and the reusable pump controller 316 can transmit the therapy data to a therapy data management system, e.g., the therapy data management system 200 in FIG. 2. Then, the therapy data management system can add the received therapy data to the blockchain and manage the therapy data as described above.

In some implementations, the diabetes management system 300 may optionally include a blood glucose meter 370 as an additional glucose sensor in addition to glucose sensor 330 (which may be a continuous glucose monitor or a flash glucose monitor), or as an alternative glucose sensor to the glucose sensor 330. In some implementations, the blood glucose meter 370 can be in wireless communication with a therapy data management system, e.g., the therapy data management system 200 in FIG. 2. In some implementations, the blood glucose meter 370 can be in wireless communication with the therapy data management system, e.g., the therapy data management system 200 in FIG, through the reusable pump controller 316 and/or mobile device 340. The blood glucose meter 370 can take a blood glucose measurement using one or more test strips (e.g., blood test strips). A test strip can be inserted into a strip reader portion of the blood glucose meter 370 and then receive the PWD's blood to determine a blood glucose level for the PWD. In some implementations, blood glucose meter 370 is configured to analyze the characteristics of the PWD's blood and generate therapy data based on the analysis. The blood glucose meter 370 further communicates (e.g., via a wired or wireless communication connection, such as NFC, RF, Short Range (e.g., BLUETOOTH®), WiFi, or other communication protocol) the therapy data to the therapy data management system, e.g., the therapy data management system 200 in FIG. 2. In some implementations, the blood glucose meter 370 can communicates the therapy data management system, e.g., the therapy data management system 200 in FIG. 2, through the reusable pump controller 316. In some implementations, a user can manually input a glucose meter reading. The blood glucose meter 370 can be manually operated by a user and may include an output subsystem (e.g., display, speaker) that can provide the user with blood glucose readings, i.e., the therapy data, that can be subsequently entered into the controller or user interface to collect the therapy data from an unconnected BGM into the system. Blood glucose meter 370 may be configured to communicate therapy data (e.g., blood glucose readings) obtained to the therapy data management system, e.g., the therapy data management system 200 in FIG. 2. In some implementations, the blood glucose meter 370 may be configured to communicate the therapy data to the therapy data management system, e.g., the therapy data management system 200 in FIG. 2, through the reusable pump controller 316 and/or other devices, such as the mobile device 340 (e.g., a control device). Such communication can be over a wired and/or wireless connection, and the data can be used by system 300 for a number of functions (e.g., calibrating the glucose sensor 330, confirming a reading from the glucose sensor 330, determining a more accurate blood glucose reading for a bolus calculation, detecting a blood glucose level when the glucose sensor 330 is malfunctioning). The therapy data management system can add the received therapy data to the blockchain and manage the therapy data as described above.

In some implementations, the system 300 includes the mobile device 340 that can communicate with the reusable pump controller 316 through a wireless and/or wired connection with the reusable pump controller 316 (e.g. NFC, RF, Short Range (e.g., BLUETOOTH®), WiFi, or other communication protocol). In some implementations, the mobile device 340 communicates wirelessly with one or more other diabetes devices of system 300. The mobile device 340 can be any of a variety of appropriate computing devices, such as a smartphone, a tablet computing device, a wearable computing device, a smartwatch, a fitness tracker, a laptop computer, a desktop computer, a PDA, a dedicated medical therapy system control device, and/or other appropriate computing devices. In some implementations (for example, where the reusable pump controller 316 does not determine a basal delivery rate), the mobile device 340 can receive and log data from other elements of the system 300 and determine basal delivery rates using methods provided herein. In some implementations, a user can input relevant data into the mobile device 340. In some implementations, the mobile device 340 can be used to transfer data from the reusable pump controller 316 to a therapy data management system, e.g., the therapy data management system 200 in FIG. 2. In some implementations, one or more methods provided herein can be performed or partially performed by the other computing device. In some implementations, the mobile device 340 provides a user interface (e.g., graphical user interface (GUI), speech-based user interface, motion-controlled user interface) through which users can provide information to control operation of the reusable pump controller 316 and/or other components in the system 300. For example, the mobile device 340 can be a mobile computing device running a mobile app that communicates with reusable pump controller 316 over short-range wireless connections as described above to provide status information for the system 300 and allow a user to control operation of the system 300 (e.g., toggle between delivery modes, adjust settings, log food intake and exercise, change a fear of hypoglycemia index (FHI), confirm/modify/cancel bolus dosages, and the like). In this example, the status information and/or the user control inputs or interactions can be the therapy data provided to the therapy data management system. For example, the mobile device 340 can be a commercial, off-the-shelf, computing device running a specialized application that provides the mobile device 340 with some or all of the specific functionality described herein. The specialized application can be, for example, an insulin delivery control application that can be used to change settings of one or more components of the system 300 (such as the insulin pump assembly 315) and display information related to medical treatments administered by the insulin pump assembly 315 and information collected by components of the system 300 such as the insulin pump assembly 315, the glucose sensor 330, and the blood glucose meter 370. In this example, the information about the settings of the one or more components of the system and the display information, the information related to medical treatments administered by the insulin pump assembly 315, and the information collected by the components of the system 300 can be the therapy data managed by the therapy data management system.

In some implementations, the system 300 may optionally include one or more manual injection devices 312 and 314 (e.g., syringes, insulin injection pens, a smart syringe with device communication capabilities, or the like) through which dosages of medication such as insulin (either or both long-acting insulin or rapid-acting insulin) or glucagon can be manually administered to a PWD. In some implementations, a suggested dosage for a bolus to be administered using the manual injection devices 312 or 314 can be output to a user via the user interface of reusable pump controller 316, on a user-interface on the manual injection devices 312 or 314, on an accessory reversibly attachable to the manual injection devices 312 or 314, and/or the user interface of the mobile device 340. In some implementations, the manual injection devices 312 or 314 can communicate through a wired and/or wireless connection with reusable pump controller 316 and/or the mobile device 340. In some implementations, system 300 can allow users to input insulin deliveries made using a syringe or insulin pen.

In some implementations, one or more computing components of the system 300 can record therapy data that is communicated to the therapy data management system 200 in FIG. 2, as described above. This therapy data can be recorded by, for example the mobile device 340, the reusable pump controller 316, the glucose sensor 330, the blood glucose meter 370, computing components of one of the manual injection devices 312 or 314, or computing components of a smart cap of one of the manual injection devices 312 or 314. In some implementations, this therapy information is transmitted by the mobile device 340, the reusable pump controller 316, or another computing component of the system 300 to a therapy data management system, e.g., the therapy data management system 200 in FIG. 2. Then, the therapy data management system can add the received therapy data to the blockchain and manage the therapy data as described above. This therapy data can be data indicating blood glucose level readings (e.g., timestamped blood glucose level readings) taken at regular or irregular intervals. The therapy data can also include medicant administration information (e.g., insulin administration information), such as information on a time that medicant was delivered by the insulin pump assembly 315 and an amount of medicant delivered by the insulin pump assembly 315 at that time. This can include tracking of both bolus and basal insulin delivery by the insulin pump assembly 315.

The therapy data can further include information related to therapy but not directly pertaining to administration of medication. For example, the therapy data can include information on meals consumed by the patient using the system 300, including time of consumption, amount of food consumed, type of food consumed, and/or caloric values, carbohydrate values, protein values, etc. for the food consumed. The therapy data can include information on physical activities (e.g., exercise) performed by the patient, including time of the physical activity, duration, intensity level, nature of the physical activity, etc. This therapy data information can be entered by the patient or care taker or automatically detected. For example, exercise can be detected by one or more accelerometers of a computing device that is part of or in communication with the system 300. For example, one or more accelerometers of a smart watch owned by the patient can convey exercise information to the mobile device 340. The mobile device 340 can then relay this exercise information to the therapy data management system 200 in FIG. 2 to record in a block chain.

In some implementations, the system 300 obtains therapy data recorded in the therapy data management system, e.g., the therapy data management system 200 in FIG. 2, to recommend therapy. For example, the system 300 obtains, from the therapy data management system, therapy data to recommend in insulin dosage, an adjustment to a basal insulin administration schedule, or food consumption. In some implementations, the system 300 can obtain the therapy data from multiple computing nodes of the therapy data management system. Since the multiple computing nodes of the therapy data management system stores the same blockchain and the blockchain stores the same therapy data, the system 300 can validate whether the therapy data obtained from the multiple computing nodes are valid by comparing them to each other. Thus, even if therapy data stored at a particular computing node is compromised, the system 300 can identify the compromise and provide uncompromised therapy data to a user, e.g., a patient or a caretaker. This improves the security of therapy data used for recommending therapy and the reliability of the system 300. In some implementations, therapy data includes glucose values (e.g., raw or estimated), sensor states (e.g., started, stopped, expired, or error), application commands (e.g., manual basal adjustments, configuration changes, notification acknowledgements, time sync, device pairing, or cannula fill), and pump responses to commands (e.g., command acknowledgements, or error responses).

Figures 4, 5A, 5B:
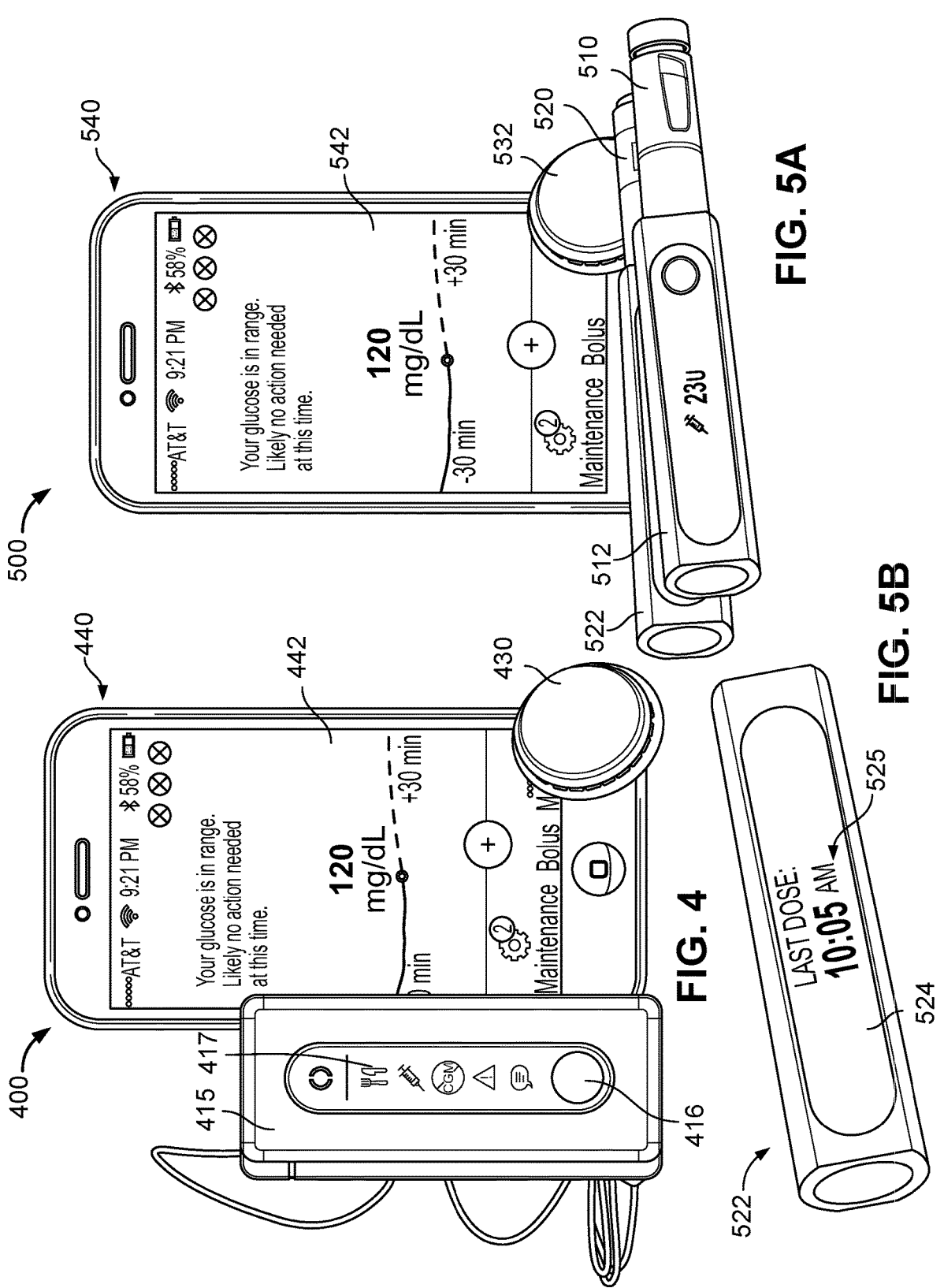
FIG. 4 illustrates an exemplary diabetes management system according to a second implementation.
FIGS. 5A and 5B illustrate an exemplary diabetes management system according to a third implementation.

FIG. 4 depicts an example therapy system that provides therapy data to a therapy data management system. For example, the therapy system may be a diabetes management system 400. The diabetes management system 400 can include a plurality of therapy related and/or non-therapy related components which can generate therapy data as described herein. The diabetes management system 400 may include fewer components than the diabetes management device of FIG. 3. As shown, a mobile device 440 can be a commercial off-the-shelf mobile device (e.g., a smartphone) and can store and execute a mobile application adapted to receive diabetes management information from insulin pump assembly 415, which can be the same as or different from insulin pump assembly 315 of FIG. 3. As shown, insulin pump assembly 415 includes a button 416 and a series of icons 417 (which may also be present on the insulin pump assembly 415), which can provide the user with status information and/or allow a user to provide instructions or confirmations directly on the insulin pump assembly 415.

Alternatively or additionally, the insulin pump assembly 415 can include additional input buttons and/or a display screen for displaying information to the user and allowing the user to provide instructions or confirmations directly on the insulin pump assembly 415. A continuous glucose monitor 430 (which may have all of the features disclosed for glucose sensor 330 of FIG. 3) is in wireless communication with the insulin pump assembly 415 and/or the mobile device 440. The mobile application can depict a graphical display 442 of blood glucose data from the continuous glucose monitor 430. In this example, the blood glucose data obtained from the continuous glucose monitor 430 can be therapy data. In some implementations, the continuous glucose monitor 430 can transmit the therapy data to a therapy data management system, e.g., the therapy data management system 200 in FIG. 2. In some implementations, the continuous glucose monitor 430 can transmit the therapy data to insulin pump assembly 415 and/or the mobile device 440 and the insulin pump assembly 415 and/or the mobile device 440 can transmit the therapy data to a therapy data management system, e.g., the therapy data management system 200 in FIG. 2. Then, the therapy data management system can add the received therapy data to the blockchain and manage the therapy data as described above with reference to FIG. 2.

FIG. 5A illustrates an example therapy system that provides therapy data to a therapy data management system. For example, the therapy system may be a diabetes management system 500. The diabetes management system 500 can include a plurality of therapy related and/or non-therapy related components which can generate therapy data as described herein. The diabetes management system 500 includes insulin injection pens 510 and 520, a glucose sensor 532 (e.g., a flash glucose monitor or a continuous glucose monitor), and a mobile device 540. The mobile device 540 can be any suitable computing device such as a smartphone, tablet, PDA, smart watch, set top box, personal computer, or a dedicated insulin delivery controller. The mobile device 540 can store and execute a mobile application that is adapted to display therapy data wirelessly received from the other components of the system.

As shown, insulin injection pens 510 and 520 respectively include pen caps 512 and 522. Each of the pen caps 512 and 522 includes one or more user interface buttons and a display. In the implementation shown in FIG. 5A, the insulin pens can be commercially mechanical insulin pens that include any suitable insulin, including long-acting insulins and rapid-acting insulins (sometimes called quick-acting insulins or ultra-fast rapid-acting insulins). Suitable rapid-acting insulins include Humalog™, Novolog™, Apidra™, Fiasp™. Suitable long-acting insulins include Lantus™, Levemir™, Toujeo™, Tresiba™. As shown, insulin injection pen 510 represents an exemplary long-acting insulin pen and insulin injection pen 520 represents an exemplary rapid-acting insulin pen. As shown, pen caps 512 and 522 can have distinct colors, shapes, or other indicia, which can be physical or digital, to assist a person with diabetes (PWD) in distinguishing the long-acting pen cap 512 from rapid-acting pen cap 522. Each of the pen caps 512 and 522 can, for example, include different software for performing different actions that are specific to long-acting and rapid-acting insulin delivery pens, respectively.

In some implementations, the pen caps 512 and 522 can take the form of another pen accessory that can be secured to each insulin injection pen. In some implementations, each of the insulin injection pens 510 and 520 can be a reusable insulin pen that includes a display or audio and/or input devices. The insulin injection pens 510 and 520 and/or caps 512 and 522 can be in wireless communication with the mobile device 540 so that therapy data from the insulin injection pens 510 and 520 and/or caps 512 and 522 can be received by and displayed by the mobile application executing on the mobile device 540. In some implementations, the insulin injection pens 510 and 520 and/or the caps 512 and 522 can transmit the therapy data to a therapy data management system, e.g., the therapy data management system 200 in FIG. 2. In some implementations, the insulin injection pens 510 and 520 and/or the caps 512 and 522 can transmit the therapy data to the mobile device 540 and the mobile device 540 can transmit the therapy data to a therapy data management system, e.g., the therapy data management system 200 in FIG. 2. Then, the therapy data management system can add the received therapy data to the blockchain and manage the therapy data as described above.

The glucose sensor 532 can be any suitable glucose sensor, such as a blood glucose meter (BGM), a flash glucose sensor, or a continuous glucose sensor (CGM). In some implementations, the glucose sensor 532 can wirelessly transmit therapy data when interrogated by a reader device (e.g., using NFC communication, RF communication, or another suitable form of wireless or wired communication). In some implementations, the glucose sensor 532 can wirelessly transmit therapy data at predetermined intervals (e.g., using radio frequencies) using any suitable communication standard (e.g., BLE).

The glucose sensor 532 can transmit therapy data, e.g., glucose data, using multiple communication techniques. In some implementations, the mobile device 540 and/or one or more of the insulin injection pens 510 and 520 or the pen caps 512 and 522 can include an NFC reader adapted to obtain blood glucose data from the glucose sensor 532 when brought within an interrogation distance of the glucose sensor 532. In these implementations, the mobile device 540 and/or the insulin injection pens 510 and 520 or the pen caps 512 and 522 can transmit the therapy data, received from the glucose sensor 532, to a therapy data management system, e.g., the therapy data management system 200 in FIG. 2. In some implementations, the glucose sensor 532 can transmit the therapy data to a therapy data management system, e.g., the therapy data management system 200 in FIG. 2. Then, the therapy data management system can add the received therapy data to the blockchain and manage the therapy data as described above.

In some implementations, the mobile device 540 and/or one or more of the insulin injection pens 510 and 520 or the pen caps 512 and 522 can wirelessly receive therapy data, e.g., blood glucose data, from the glucose sensor 532 that is broadcast at predetermined periods of time (e.g., every minute, every 5 minutes, etc.).

When using exemplary diabetes management system 500, a PWD (or their caregiver) would be responsible for determining when to inject insulin and how much to inject, but system 500 could assist the PWD (or caregiver) in determining an appropriate insulin dose based on current data from the glucose sensor, based on stored therapy parameters, and/or based on data about insulin injections. In some implementations, the pen caps 512 and 522 (or alternatively the pens themselves) can provide therapy data about when the last insulin injection was made. For example, the pen caps 512 and 522 can generate therapy data by detecting a time at which the respective cap 512 and 522 has been reapplied to its insulin injection pen 510 and 520, which can be assumed to be the time of an injection administered to the PWD. In some implementations, the pen caps 512, 522 can generate therapy data by tracking remaining insulin in an insulin injection pen and determining an amount of each dose. In some implementations, smart pens or pen accessories can detect the dosages set or administered using other suitable techniques. In these implementations, the therapy data can be transmitted from the pen caps 512 and 522 to a therapy data management system, e.g., the therapy data management system 200 in FIG. 2. Then, the therapy data management system can add the received therapy data to the blockchain and manage the therapy data as described above.

In some implementations, such as shown in FIG. 5B, the pen cap 522 (or a smart pen or other pen accessory) can depict a time 525 of the most recent dose, or "last dose" on a display 524 which can assist a user in remembering if they have bolused for a recent meal and help a user avoid an unintentional stacking of boluses. In some implementations, such as in situations in which the pen caps 512 and 522 are capable of detecting an amount of a dose, the display 524 can additionally display the number of units of the last dose. In some implementations, the timing of the last dose can include a time zone obtained from the mobile device 540. In some implementations, the display 524 might depict a most recently obtained blood glucose level and the time it was obtained. In some implementations, the display might be an electronic ink display. In some implementations, the display can include identifying information (e.g., a label such as "Sarah's pen") and/or information about the type of insulin pen that it is attached to (e.g., the brand of insulin, or an indicator of rapid or slow acting insulin). In some implementations, a notice icon can appear on the pen caps 512 and 522 in order to indicate to the user that a more detailed suggestion, tip, alert, or alarm is available for the user to view in the mobile application on the mobile device 440.

Figure 6:
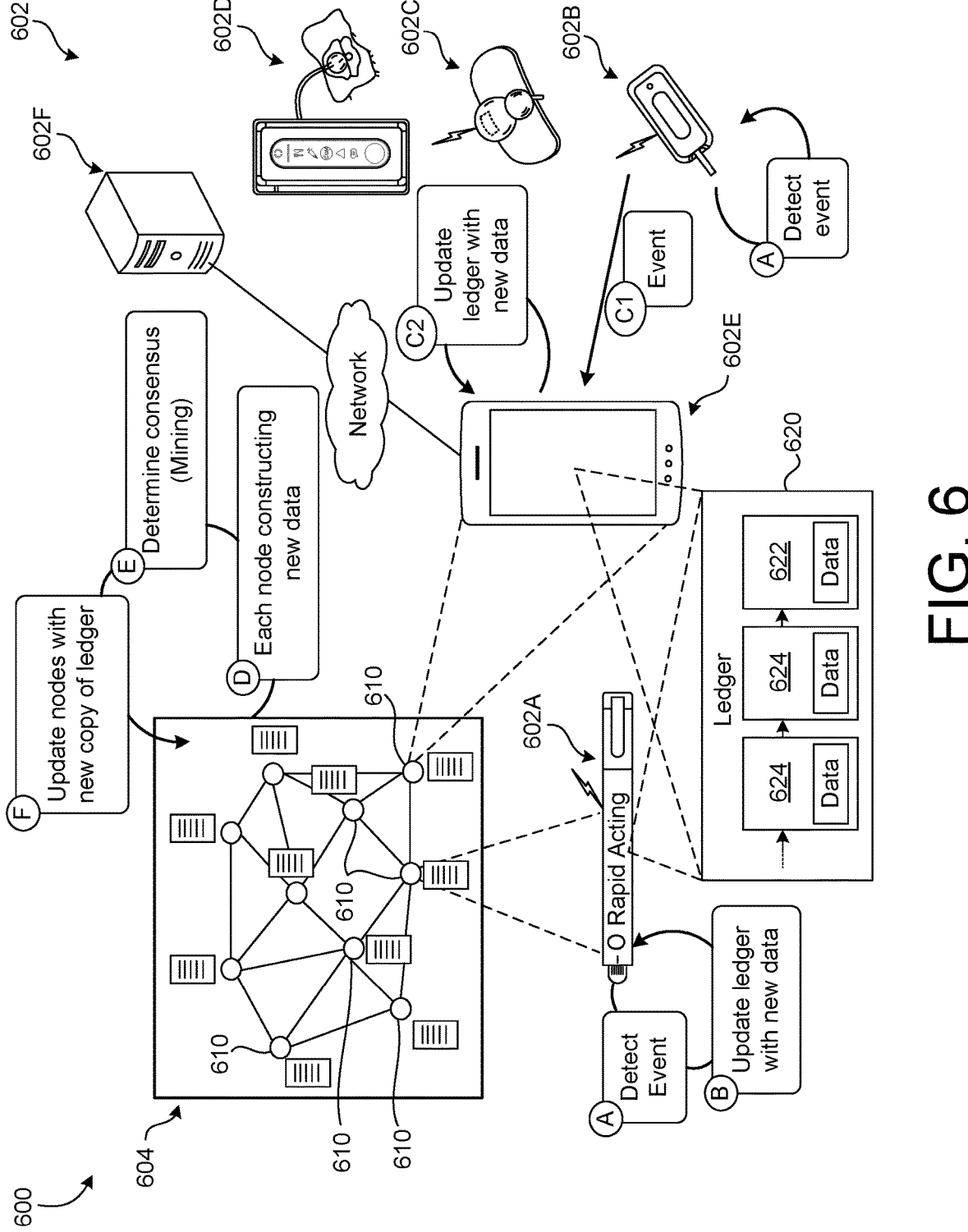
FIG. 6 illustrates an example therapy data management system.

FIG. 6 illustrates an example therapy data management system 600. In this example, the therapy data management system 600 is configured for a diabetic management system. The therapy data management system 600 can include a plurality of therapy related and/or non-therapy related components 602 which can generate therapy data and record the therapy data in a distributed ledger system 604. Examples of the components 602 can include an injection device 602A, a blood glucose meter 602B, a continuous glucose meter 602C, an insulin pump assembly 602D, a user computing device 602E, and a remote management server 602F. The components 602 may be similar to the components described in FIGS. 3-5.

One or more of the components 602 in the system can be computing nodes 610 in a distributed ledger system 604. In addition, one or more of the components 602 in the system are not capable of functioning as computing nodes 610, and thus record data in a distributed ledger through one or more intermediate devices, such as other components 602 or other suitable computing devices.

In general, computing nodes 610 in a distributed ledger system 604 can be any active electronic device, including a computer, phone, or other devices with processing capability. Computing nodes are connected to the Internet and have an IP address. Computing nodes support the network by maintaining a copy of a ledger and, in some cases, to process transactions. Computing nodes may be arranged in the structure of trees, known as binary trees. A computing node can either be a communication endpoint or a point of communication redistribution, linking to other nodes. Every computing node on the network is considered equal, however certain nodes have different roles in the manner in which they support the network. For example, not all computing nodes store a full copy of a ledger or validate transactions. A full node downloads a complete copy of a ledger and checks any new transactions (e.g., therapy data) coming in based on the consensus protocol utilized in the system. All nodes use the same consensus protocol to remain compatible with each other. It is the nodes on the network that confirm and validate transactions, putting them into blocks. Each node comes to its own conclusion on whether a transaction is valid and should be added to a block with other transactions, irrespective of how other nodes act.

The components 602 can record therapy data on a distributed ledger directly or via an intermediate. For example, the components 602 (e.g., the injection pen 602A), acting as computing nodes 610, can record therapy data in a distributed ledger system 604. Alternatively, a component 602 can record therapy data through another component 602 or a third party device which acts as a computing node 610. In the illustrated example, a blood glucose meter 602B is connected to the user computing device 602E via a wireless communication protocol (e.g., Bluetooth or NFC), and can transmit therapy data to the user computing device 602E. The user computing device 602E, functioning as a computing node 610, records the therapy data onto a ledger in a distributed ledger system 604.

The components 602 in a therapy system can generate therapy data during operation or in use. For example, therapy data can include information about one or more events resulting from operation of a component 602, such as medicant injection, glucose level detection, user control inputs, setting, or other interactions with the component, etc. In addition or alternatively, therapy data can include data associated with the events, such as data detected by a component 602 (e.g., dosage injected, blood glucose level, etc.), transmission and reception of data, which component receives data, which component transmits data, timing of data transmission or reception, etc.

Various types of events can be detected and recorded as various types of therapy data, including information directly pertaining to medication administration, measured patient information (e.g., vital signs, blood glucose levels) and other therapy related data. By way of example, therapy related data can include a glucose value obtained by a glucose meter, a glucose value transmitted between components (e.g., from a glucose meter to a mobile device, from a glucose meter to a pen cap, etc.), a time that a pen cap is removed from a pen for injection, an amount of insulin delivered, an amount of carbohydrate recorded as ingested, etc. As additional examples, therapy related data can include user interactions with components, such as which button is pressed, which area is selected on a touchscreen, what settings are adjusted, etc.

The therapy data recorded in a distributed ledger can be traced to objectively identify or infer the cause of an issue in a therapy system, and determine liability among different components (and/or different parties) in the therapy system. This can permit multiple parties associated with a therapy system (e.g., different component manufacturers, suppliers, healthcare practitioners and clinics, patients, etc.) to have higher confidence with their partners (e.g., other parties in the therapy system) and allow reliable interoperability between them. Further, such traceability of therapy data in the distributed ledger can ensure safety in the operations of different components. By way of example, when a patient replaces an existing glucose meter with a new glucose meter from a different manufacturer, a distributed ledger retains a seamless record of not only the therapy data from the existing glucose meter but also therapy data from the new glucose meter, thereby providing confidence about the record of the patient's glucose level to all different parties that are interested in the patient's glucose monitoring, and promoting different manufacturers of glucose meters to make their products that operate in reliable and compatible ways. In another example, the therapy data can include information about the supply chain in the history to determine the provenance of those supplies (e.g., based on lot numbers, manufacturers, etc.). The therapy data can be traced to find faulty supplies, such as faulty infusion sets, insulin, etc.

Referring still to FIG. 6, an example process of managing therapy data from a therapy system in a distributed ledger system is described. In some implementations, a component 602 (e.g., a first component 602A and a second component 602B) detects an event (Step A). Such an event can be associated with operation of the component 602. For example, an event can include an injection of insulin from an injection pen 602A.

The component 602 (e.g., the first component 602A), acting as a computing node 610, can operate to record data relating to the event by updating a ledger with the data (Step B). In addition or alternatively, if the component 602 (e.g., the second component 602B) is not capable of operating as a computing node 610, the component 602 transmits data relating to the event to one or more intermediate devices which can work as computing nodes 610 (Step C1). For example, the user computing device 602E can be used as an intermediate device. Then, similarly to Step B, the intermediate device (e.g., the user computing device 602E) operate to record the data by updating a ledger with the data (Step C1).

The data relating to the event can include various pieces of information about the event, such as measurements obtained by the component, the identification of the component, a destination device or component to which data is transmitted, a timestamp of the measurements obtained, a timestamp of data being transmitted.

In some implementations, the data can be transmitted to and recorded onto a distributed ledger with message authentication code to ensure data integrity and authentication of the component. Various cryptographic signatures can be used. For example, when recording data, a computing node can create a cryptographic signature that contains an identifier of the component that has transmitted the data. Alternatively or in addition, a manufacturer of a component may generate a pair of private and public keys for a component 602. The manufacturer of that component can keep the private key and distribute the public key to other parties in the system to verify integrity of the data coming from the component, and/or authentication of the component 602. In some implementations, a hash-based message authentication code (HMAC) can be used which involves a cryptographic hash function and a security cryptographic key. Other message authentication code or cryptographic signature schemes can be used in other implementations.

In some implementations, the computing nodes 610, such as the first component 602A and the user computing device 602E in this example, can update a distributed ledger 620 with the data (Steps B and C2) by providing the ledger 620 with a new block 622 that contains the data and will be associated with a chain of existing blocks 624 in the same or similar manner as described in FIGS. 1 and 2.

Each of at least some of the other computing nodes 610 in the distributed ledger system 604 operates to construct a new block of data on the distributed ledger (Step D). Such new blocks can be constructed with cryptographic keys and signatures. Then, the at least some of the other computing nodes 610 in the system use a consensus algorithm to vote on which copy is correct (Step E). Once consensus is made on the new block's validity, the at least some of the other computing nodes 610 operate to update the distributed ledgers with a new copy of the ledger (Step F).

Figure 7:
FIG. 7 is a flowchart of an example process for tracing operations of components in a therapy system.
Figure 7:
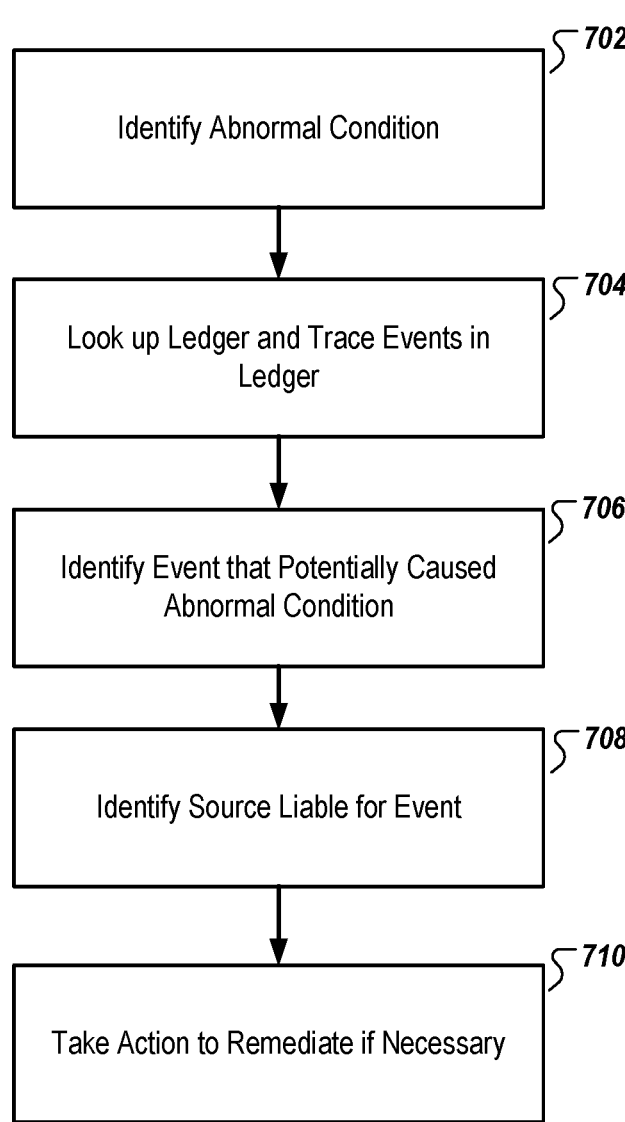

FIG. 7 is a flowchart of an example process 700 for tracing operations of components in a therapy system. Some embodiments of the distributed ledger system described herein permit for parties (e.g., component manufacturers, healthcare practitioners or entities, patients, etc.) to retrieve the therapy data recorded in the ledger and trace the operations of the components in the therapy system and their contributions to the therapy system, thereby allowing the parties to objectively identify any abnormal behavior or suspicious operations from any of the components in the system. Such identification of abnormal behavior or suspicious operation of components can be used to identify a liable/faulty component or party (e.g., manufacturer, supplier, healthcare practitioner, user, etc.) and properly remediate the issue.

One or more computing devices, such as the components in a therapy system as described herein and/or other remote computing devices, can be used to perform at least part of the process 700. Such computing devices can communicate with each other or other computing devices via one or more communication interfaces, such as wired or wireless direct communications, broadband networks, cellular networks, or other suitable communication networks, as described herein. For example, one or more components in a therapy system, such as the components 602A-F (FIG. 6), can perform at least part of the process 700 either individually and/or by communicating with other components in the therapy system or other remote computing devices, such as one or more computing nodes in a distributed ledger system. A single computing device (e.g., one of the components 602A-F described in FIG. 6) can perform the process 700. Alternatively, a group of networked computing devices, (e.g., two or more of the components 602A-F described in FIG. 6) can perform the process 700 by communicating with each other.

In some implementations, an abnormal condition is identified (Block 702). Such an abnormal condition can be of various types and/or result from various causes. For example, an abnormal condition can be associated with a patient, such as an undesired blood glucose measurement for a patient. In addition or alternatively, an abnormal condition can include component-related conditions, such as malfunction, undesired or unintended settings, or miscalibration of a component. An example abnormal condition is where a CGM reading and a BGM reading do not agree for a patient. Another example abnormal condition may be identified if two different glucose meters provide different measurements from a patient at a given point of time (e.g., a difference outside a specified range). Such a discrepancy in the measurements may result from one or more various sources, such as when one or more parts of either of the glucose meters had problems that need to be repaired, when either of the glucose meters was not properly used by the patient or caregiver, when either of the glucose meters had inappropriate settings, and/or when other components in the system were malfunctioned or had issues.

As another example, one or more blood glucose readings may indicate that an insulin delivery (e.g., a bolus or basal delivery) that was indicated as previously delivered by an insulin pump was not actually delivered properly (e.g., due to a malfunction with the insulin delivery pump). Such an error could occur due to a software fault by the insulin delivery pump, an occlusion in the insulin delivery line, a malfunction of the drive system of the insulin delivery pump, faulty settings for the insulin delivery pump, or one or more other errors.

The distributed ledger is looked up to trace one or more events therein (Block 704). A computing device, which can operate as a computing node or has access to a computing node, can be used to retrieve the therapy data recorded in the ledger. For example, one or more of the components in the therapy system can be used to access the ledger and retrieve the therapy data recorded therein. Such a computing device can process the therapy data and present (e.g., display) to a user a history of the events and other associated information in a human-readable format. Alternatively, a computing device can process the therapy data, and automatically identify one or more events relative to the abnormal condition and output information about such events to a user.

One or more events are identified which actually or potentially caused the abnormal condition (Block 706). In some implementations, a user can manually review the history of events and associated information and identify any undesired or unexpected event therefrom. In addition or alternatively, a computing device can automatically determine any undesired or unexpected results from the events recorded in the ledger and present the determination to a user. In some implementations, one or more rules can be provided for identifying undesired or unexpected operations, functions, settings, and/or behaviors of components and/or humans using the components, and/or identifying undesired or unexpected measurements about patient's physiological or body conditions (e.g., glucose levels, etc.).

One or more sources are identified which are actually or potentially liable for the identified events (Block 708). Such liable sources can include one or more of the components (e.g., suspicious component(s)) in the therapy system, which have malfunctioned, had undesired or unintended settings, have been miscalibrated, etc. In addition, the manufacturers of the identified components and/or the associated LOT numbers can be also identified. Alternatively or in addition, the liable sources can include improper behaviors of the patient or caregivers, such as human errors in operating the components, entering settings, manually administering medication, or recording information (e.g., manual insulin delivery, food consumption, physical activity).

One or more are actions are taken to remediate the abnormal condition if necessary (Block 710). Various actions can be selectively taken depending on, for example, the type of abnormal condition, identified events, and identified sources of the events. In some implementations, the component that is identified as the source of the abnormal condition can be stopped in operation. For example, the identified component can be manually stopped by a user who receives an alert from a computing device (e.g., the computing device used to record and/or access the ledger). Alternatively, the identified component can be automatically stopped or paused in response to a signal transmitted from a computing device (e.g., the computing device used to record and/or access the ledger). In other implementations, the identified component can be removed from the therapy system, or replaced with a new component.

In some implementations, a user (e.g., the patient or caregiver) is prompted to take an appropriate action to remediate the abnormal condition. The user can receive an alert via one or more of the components in the therapy system or other computing devices, and be informed of the abnormal condition and its cause so that the user can take a voluntary action to fix the condition, for example by injecting an increased dosage of insulin, injecting an instructed dosage of glucagon, by taking certain food, by performing instructed exercises, by adjusting settings on one or more of the components in the therapy system, by stopping operation of, removing, repairing, or replacing one or more of the components in the therapy system, etc. The user can also be prompted to seek professional help, e.g., from a doctor or from a technician who can repair or replace a faulty component.

In some implementations, the computing device used to record and/or access the ledger for analysis can further generate a notification (e.g., an alert) and output the notification to the user. Alternatively, the computing device can transmit the notification to another computing device so that such other computing device outputs the notification to the user. The notification can include various pieces of information, such as the indication of abnormal condition, associated events, and sources of the events, and the indication of actions required to be taken by the user and/or actions to be performed by one or more components or other devices to fix the abnormal condition.

In some implementations, the computing device used to record and/or access the ledger can reject data from the component(s) identified as untrusted or unverified, so that such data is not recorded, or does not attempt to be recorded in the ledger. For example, a certificate signed by an authority can be revoked so that the associated component can no longer participate in the system. In another example, a public key that has been given to the manufacturer of the component that caused an abnormal condition can be revoked so that the component or other components provided by the manufacturer is not allowed to join the distributed ledger system and is prevented from providing any data into the distributed ledger.

The features described in this disclosure can be implemented in digital electronic circuitry, or in computer hardware, firmware, software, or in combinations of them. The systems and apparatus described herein can be implemented in a computer program product tangibly embodied in an information carrier, e.g., in a machine-readable storage device, for execution by a programmable processor; and method steps can be performed by one or more programmable processors executing one or more programs of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing context.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer (e.g., desktop, laptop, server, etc.) or other computing device (e.g., smartphone, tablet, PDA, smart watch, set top box, specialized medical device, or another specialized computing device) having a display device such as a CRT (cathode ray tube), LCD (liquid crystal display), plasma, or other display screen for displaying information to the user and a keyboard, a pointing device such as a mouse or a trackball, a touch screen, input buttons, or other input hardware by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Nevertheless, it will be understood that various modifications may be made without departing from the spirit and scope of the invention. For example, various forms of the flows shown above may be used, with steps re-ordered, added, or removed. Also, although several applications of the payment systems and methods have been described, it should be recognized that numerous other applications are contemplated. Accordingly, other implementations are within the scope of the following claims.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some implementations be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some implementations, multitasking and parallel processing may be advantageous.

What is claimed is:

1. A method for managing therapy data related to diabetes treatment of a user using a plurality of computing nodes, wherein each of the plurality of computing nodes is associated with a respective blockchain, the method comprising:

sending, by a first medical device of a user to a first computing node of the plurality of computing nodes, first therapy data related to the diabetes treatment of the user, the first computing node being associated with a first blockchain;

validating, at the first computing node, the first therapy data using at least one of a plurality of features associated with the first blockchain;

in response to validating the first therapy data using at least one of the plurality of features associated with the first blockchain, adding the first therapy data to the first blockchain;

receiving a request from a second medical device of the user to obtain the first therapy data from the first blockchain, wherein the second medical device is replacing the first medical device and is configured to obtain the first therapy data from multiple ones of the plurality of computing nodes including the first computing node;

in response to receiving the request, providing, by the first computing node the first therapy data to the second medical device;

comparing, by the second medical device, the first therapy data with each other and, if the comparison shows that the first therapy data obtained from the multiple ones of the plurality of computing nodes are identical, validating the first therapy data, wherein the first medical device includes a glucose sensor that detects glucose or another analyte in interstitial fluid and the therapy data includes blood glucose level;

upon identifying an abnormal condition based on the comparison or validation, automatically performing a corrective action comprising at least one of: transmitting, by the first computing node, a control signal to a control device of an insulin pump to adjust a basal insulin delivery rate or halt pump operation; or transmitting, by the first computing node, a control signal to stop operation of a suspicious component; and controlling either the insulin pump or stopping the operation of the suspicious component in response to receipt of the control signal.

2. The method of claim 1, wherein the first and second medical devices are the same medical device.

3. The method of claim 1, wherein validating the first therapy data using at least one of the plurality of features associated with the first blockchain comprising:

in response to obtaining the first therapy data, broadcasting, by the first computing node to at least one of the plurality of computing nodes other than the first computing node, the first therapy data, and verifying, by the at least one of the plurality of computing nodes other than the first computing node, that the first therapy data are valid.

4. The method of claim 3, wherein verifying, by the at least one of the plurality of computing nodes other than the first computing node, that the first therapy data are valid comprising:

obtaining a first value for at least one of the plurality of features associated with the first blockchain, identifying a second blockchain associated with the at least one of the plurality of computing nodes other than the first computing node, obtaining a second value for at least one of the plurality of features associated with the second blockchain, and comparing the first value to the second value.

5. The method of claim 4, wherein the first value is a nonce value for the first blockchain and the second value is a nonce value for the second blockchain.

6. The method of claim 1, wherein the first medical device includes a glucose sensor that detects glucose or another analyte in interstitial fluid, and the therapy data includes blood glucose level.

7. The method of claim 1, further comprising:
obtaining, by the first computing node from the first medical device, second therapy data;
determining, by the first computing node, whether the second therapy data are within a range from a reference value; and
in response to a determination that the second therapy data are out of the range from the reference value, providing a signal by the first computing node to the first medical device or a control device of the first medical device.

8. The method of claim 7, wherein the plurality of blockchains respectively associated with the plurality of computing nodes identify the same therapy data.

9. The method of claim 7, wherein determining whether the second therapy data are within the range comprises comparing the second therapy data with therapy data in at least another one of the plurality of computing nodes.

10. The method of claim 7, wherein the signal is configured to cause the first medical device to stop.

11. The method of claim 7, wherein the signal is configured to present a warning to a user of the first medical device.

12. The method of claim 1, wherein the first medical device is one of the computing nodes of the plurality of computing nodes, wherein the first medical device does not implement an entire blockchain protocol.

13. The method of claim 12, wherein the first medical device functions exclusively to send and receive data with regard to other ones of the plurality of computing nodes in a distributed ledger system.

14. The method of claim 1, wherein validating the first therapy data by the first computing node comprises using a mining node.

15. The method of claim 1, wherein the first computing node is a component in a diabetes management system.

16. The method of claim 1, wherein the first medical device is an existing glucose meter for a patient, and wherein the second medical device is a new glucose meter for the patient that replaces the existing glucose meter, the new glucose meter being from a different manufacturer than the existing glucose meter.

17. The method of claim 1, wherein the first therapy data includes information on a supply chain of the first medical device.

18. A system comprising:
a first medical device for providing diabetes treatment to a user;

a second medical device for providing diabetes treatment to the user, wherein the second medical device is a replacement of the first medical device; and
a plurality of computing nodes implemented using respective processors executing instructions in memory, each of the plurality of computing nodes associated with a respective blockchain that identifies therapy data and that is associated with a plurality of features, wherein a first computing node of the plurality of computing nodes is configured to:
obtain first therapy data from the first medical device, the first computing node being associated with a first blockchain,
validate the first therapy data using at least one of the plurality of features associated with the first blockchain,
add the first therapy data to the first blockchain in response to validating the first therapy data using at least one of the plurality of features associated with the first blockchain; and
wherein the second medical device, upon replacement of the first medical device, is configured to:
obtain the first therapy data from multiple ones of the plurality of computing nodes including the first computing node,
compare the obtained first therapy data with each other,
validate the obtained first therapy data if the comparison shows that the first therapy data obtained from the multiple ones of the plurality of computing nodes are identical, and
in response to validation of the first therapy data, use the first therapy data to provide, via a display device of the second medical device, a patient therapy recommendation and diabetes treatment; and
upon identifying an abnormal condition, the system is configured to automatically perform a corrective action comprising at least one of adjusting an insulin pump delivery rate, halting pump operation, stopping operation of a suspicious component.

19. The system of claim 18, wherein the first medical device is one of the computing nodes of the plurality of computing nodes, wherein the first medical device does not implement an entire blockchain protocol.

20. The system of claim 18, wherein the first medical device is an existing glucose meter for the user, and wherein the second medical device is a new glucose meter for the user that replaces the existing glucose meter, the new glucose meter being from a different manufacturer than the existing glucose meter.

* * * * *